(12) United States Patent
Nitsche

(10) Patent No.: US 11,678,803 B1
(45) Date of Patent: Jun. 20, 2023

(54) SYSTEM AND METHOD FOR IMPROVED MEASUREMENT OF PEAK INTENSITIES IN PULSE HEIGHT SPECTRA OBTAINED BY WAVE-LENGTH DISPERSIVE X-RAY FLUORESCENCE SPECTROMETERS

(71) Applicant: Bruker AXS GmbH, Karlsruhe (DE)

(72) Inventor: Fabian Nitsche, Wörth am Rhein (DE)

(73) Assignee: Broker AXS GmbH, Karlsruhe (DE)

( * ) Notice: Subject to any disclaimer, the term of this patent is extended or adjusted under 35 U.S.C. 154(b) by 0 days.

(21) Appl. No.: 18/160,656

(22) Filed: Jan. 27, 2023

(30) Foreign Application Priority Data

Feb. 1, 2022 (EP) .................................. 22154483

(51) Int. Cl.
*A61B 5/00* (2006.01)

(52) U.S. Cl.
CPC .................................. *A61B 5/0075* (2013.01)

(58) Field of Classification Search
CPC .................................................... A61B 5/0075
See application file for complete search history.

(56) References Cited

U.S. PATENT DOCUMENTS

| | | | |
|---|---|---|---|
| 6,310,935 B1 | 10/2001 | Kuwabara | |
| 2017/0184519 A1* | 6/2017 | Sako | ........................ G01T 1/40 |
| 2019/0064084 A1* | 2/2019 | Ullom | ........................ G01T 1/36 |
| 2021/0131983 A1* | 5/2021 | Ogoshi | .............. G01N 23/2252 |

FOREIGN PATENT DOCUMENTS

| | | |
|---|---|---|
| EP | 1978354 A1 | 10/2008 |
| EP | 3835769 A1 | 6/2021 |

OTHER PUBLICATIONS

European Search Report for Application No. 22154483.6, dated Jul. 4, 2022, 6 pages.

(Continued)

*Primary Examiner* — Hugh Maupin
(74) *Attorney, Agent, or Firm* — Brake Hughes Bellermann LLP

(57) ABSTRACT

Techniques for estimating peak intensities in pulse height spectra obtained by a wave-length dispersive x-ray fluorescence spectrometer are disclosed. A pulse height spectrum is obtained from a sample. A model generator generates a pulse height spectrum model by creating a plurality of diffraction order profiles with predefined profile shapes at photon energy positions corresponding to respective diffraction orders of a monochromator of a spectrometer. For each created diffraction order profile where the corresponding photon energy is higher than the edge energy of the detector material of the detector, a respective escape profile is added. A model adjustment module adjusts pulse-height-to-energy-mapping parameters and contribution area of each diffraction order profile ensemble of the pulse height spectrum model using a fitting algorithm. An intensity module provides the contribution area of the first order profile ensemble as the intensity of the energy to be determined by the wavelength-dispersive X-ray fluorescence spectrometer.

20 Claims, 12 Drawing Sheets

(56) References Cited

OTHER PUBLICATIONS

W. Guo et al., "The Monte Carlo Approach MCPUT for Correcting Pile-Up Distorted Pulse-height Spectra", Elsevier; Nuclear Instruments and Methods in Physics Research, vol. 531, No. 3; Oct. 2004, pp. 520-529.

E. De Pauw et al., "Highly Sensitive Nondestructive Rare Earth Element Detection by Means of Wavelength-Dispersive X-Ray Fluorescence Spectroscopy Enabled by an Energy Dispersive PN-Charge-Coupled-Device Detector", Analytical Chemistry, vol. 92, No. 1, Jan. 7, 2020, pp. 1106-1113.

\* cited by examiner

SYSTEM AND METHOD FOR IMPROVED MEASUREMENT OF PEAK INTENSITIES IN PULSE HEIGHT SPECTRA OBTAINED BY WAVE-LENGTH DISPERSIVE X-RAY FLUORESCENCE SPECTROMETERS

CROSS-REFERENCE TO RELATED APPLICATIONS

This application claims priority to EP Patent Application No. 22154483.6, filed on Feb. 1, 2022, and entitled "System and method for improved measurement of peak intensities in pulse height spectra obtained by wave-length dispersive x-ray fluorescence spectrometers," the disclosure of which is hereby incorporated by reference in its entirety.

TECHNICAL FIELD

The present description generally relates to wave-length dispersive x-ray fluorescence spectroscopy, and more particularly relates to separating analytically relevant information from multiple signals contained in a pulse height spectrum of a multi-channel analyzer used by wave-length dispersive x-ray fluorescence spectrometers.

BACKGROUND

In wave-length dispersive x-ray fluorescence spectroscopy, an x-ray tube generates polychromatic radiation including characteristic lines and Bremsstrahlung. The radiation is directed on a sample to be analyzed. The radiation generates polychromatic x-ray fluorescence and scattered radiation in the sample. In a wavelength-dispersive x-ray fluorescence spectrometer, the radiation emitted by the sample is analyzed by measuring, with a goniometer, the radiation reflected by a monochromator of the spectrometer (typically a crystal) at various diffraction angles θ. This technique is based on Bragg's law $$n\lambda = 2d \sin \theta, \tag{F1}$$

where n is the diffraction order, λ the wavelength and d the lattice plane distance of the monochromator.

If n=1, only a single wavelength (the analytical signal) can reach the detector. However, the diffraction order may be higher than one, allowing also shorter wavelengths (higher energies) to reach the detector:

$$2\, d \sin \theta = \lambda_1 = 2\frac{\lambda_1}{2} = 2\, \lambda_2 = 3\frac{\lambda_1}{3} = 3\, \lambda_3 \text{ with } \lambda_2 = \frac{1}{2}\lambda_1, \tag{F2}$$

$$\lambda_3 = \frac{1}{3}\lambda_1, \ldots \text{ or } E_2 = 2\, E_1, E_3 = 3\, E_1,$$

Consequently, x-ray photons of multiples of the energy of the analytical signal $E_1$ arrive at the detector.

When a photon hits the detector of the spectrometer, the photon is eventually converted into an electric pulse where the pulse height is proportional to the energy of the photon. However, with the initial absorption of the x-ray photon, the detector material itself generates fluorescence radiation that can leave the detector and thus diminishes the pulse height registered (measured) by the detector. This is called escape and causes an additional peak at lower energies in the pulse height spectrum.

Additionally, if a second x-ray photon of the same energy hits the detector before the detector is done registering the first photon, the pulses are partially or fully added up and generate a feature in the pulse height spectrum that is centered at two times the original energy and that is called pile-up.

Additional effects may contribute to the pulse height spectrum that further complicate and interfere with the determination of the analytical signal. The detector itself adds background noise, the crystal may add its fluorescence signals, and the aging of the detector may cause a change of the peak shape and position in the spectrum.

In the pulse height spectrum for said sample, obtained by a multi-channel analyzer of the spectrometer, the measured peaks result from multiple overlapping signal components originating from different diffraction orders related to the structure of the monochromator. In other words, there is a problem to derive the correct intensity of the analytical signal from the measured pulse height spectrum. Prior approaches typically use a fixed integration region to estimate the intensity of the first order peak from the measured pulse height spectrum. However, due to the superposed contribution of higher diffraction orders inside such a fixed integration region, the problem to separate such contributions from the intensity of the first order peak leads to inaccurate estimates.

SUMMARY

There is therefore a need for systems and methods that provide the intensity of the analytical signal at the energy to be determined by a wavelength-dispersive X-ray fluorescence spectrometer.

Embodiments of the description as claimed in the independent claims include a computer-implemented method, computer system and computer program product for estimating peak intensities in pulse height spectra obtained by wave-length dispersive X-ray fluorescence spectrometers—in particular to determine the contribution of the first diffraction order in the obtained pulse height spectrum. It is to be noted that in some embodiments, the computer system may be an integrated component of the wave-length dispersive X-ray fluorescence spectrometer. In other embodiments, the computer system is communicatively coupled with the wave-length dispersive X-ray fluorescence spectrometer.

In one aspect, this is achieved when executing the computer program product by a computer system to perform said computer-implemented method. Initially, the computer system receives a pulse height spectrum obtained by a multi-channel analyzer (MCA) of a wavelength-dispersive X-ray fluorescence spectrometer from a sample. Digital interfaces adapted to receive pulse height spectra from MCAs by a computer system are well known. The received pulse height spectrum includes a plurality of peaks which typically reflect a superposition of different signal components originating from different diffraction orders as described in the background section. In the context of this disclosure, the term "peak" refers to a portion of a measured pulse height spectrum (i.e., a portion of the respective measured graph) in the vicinity of a local maximum of that measured graph.

A model generator of the computer system generates a pulse height spectrum model (PHSM). To distinguish measured peaks from local maxima in the PHSM, this disclosure uses the term "profile" to refer to a component contributing to the composition of the PHSM. A component may also have a local maximum similar to a peak, but other component shapes are possible, too. The PHSM includes at least two different types of profiles: diffraction order profiles and escape profiles.

The model generator creates a plurality of diffraction order profiles with predefined profile shapes at photon energy positions corresponding to respective diffraction orders of a monochromator of the spectrometer. For example, Gaussian shaped profiles may be used. But alternative shapes, such as Lorentzian shapes, Voigt shapes or pseudo-Voigt shapes may be used as well. The photon energy positions are determined by the Bragg equation and the diffraction properties of the monochromator. The model generator determines the widths of the diffraction profiles by using a calibrated width model reflecting dependencies of the widths on respective energy positions and total incoming count rates of the detector of the spectrometer. The relative positions of the diffraction profiles are determined by their respective energies and a mapping of pulse heights to corresponding energy values. A photon which is captured by the detector generates an electric pulse from which only the pulse height is evaluated. The higher the photon energy, the higher the measured electric pulse. The mentioned pulse-height-to-energy mapping describes the correlation between the photon energy and the height of the respective electric pulse.

The model generator further adds escape profiles to the PHSM where appropriate. This is the case for each previously created diffraction order profile where the corresponding photon energy is higher than the edge energy of the detector material. The respective escape profile is added to the PHSM at the position of the photon energy of the respective diffraction order profile diminished by the fluorescence energy of the photon escaped from the detector material. The intensity of the escape profile is determined by using a calibrated escape intensity model reflecting dependencies of the intensity on respective energy positions. For gas detectors the escape intensity model may also depend on the gas pressure. Escape profiles of higher diffraction orders typically overlap with the first order diffraction profile.

The generated PHSM together with the received (measured) pulse height spectrum serve as inputs for a model adjustment module (MAM) of the computer system. The MAM adjusts pulse-height-to-energy-mapping parameters and contribution area of each diffraction order profile ensemble of the PHSM. This is achieved by using a fitting algorithm to minimize the difference between the PHSM and the measured pulse height spectrum. Thereby, the PHSM and the measured spectrum may be weighted or Anscombe transformed. For example, certain detector regions are dominated by electronic noise and can be weighted with zero whereas the other regions may be weighted with one or the inverse of the error. A skilled person may use other weightings as well. The term "diffraction order profile ensemble" as used herein denotes all generated profiles associated with a respective diffraction order. For example, the superposition of the first order diffraction profile and the pile-up profile may be referred to as the first order profile ensemble (if no escape profile has been generated for the first order). The superposition of the second order escape profile and the second order diffraction profile may be referred to as the second order profile ensemble (in the absence of further profile types), and so on. The pulse-height-to-energy-mapping parameters include the following two parameters: slope and offset. The contribution area of a particular diffraction order ensemble is the integral of the graph resulting from the superposition of all profiles associated with the particular diffraction order.

An intensity module of the computer system finally provides the contribution area of the first order profile ensemble as the intensity at the energy to be determined (i.e., measured) by the wavelength-dispersive X-ray fluorescence spectrometer. In other words, the intensity of the analytical signal in the measured pulse height spectrum corresponds to the contribution area of the first order profile ensemble which can be accurately determined after fitting the PHSM to the measured pulse height spectrum in the adjusting step. Typically, a least-squares fitting algorithm can be used as the fitting algorithm. However, a person skilled in the art may also use other appropriate fitting algorithms. In general, the intensity of the analytic signal at the to-be-determined energy (i.e., the contribution area of the first order profile ensemble) is the sum of the first order profile intensity, the escape profile intensity (if an escape profile has been generated for the first order profile ensemble) and the intensity of the pile-up profile multiplied by a correction factor. For example, a correction factor of two may be used because typically each pulse in the pile-up is based on actually two pulses. However, the correction factor may also be more complex. Properly adding the pile-up profile to the first order diffraction profile ensemble by using the correction factor significantly increases the linearity of the detector (up to tripling the linearity).

As described earlier, a measured pulse height spectrum may suffer from further signal components which make the measurement of the analytical signal intensity difficult. One of these further signal component types is the so-called pile-up. Therefore, the model generator may add a pile-up profile to the first order diffraction profile. The intensity of the pile-up is determined by using a calibrated pile-up intensity model reflecting the dependencies of pile-up intensity on the respective energy position (of the first order diffraction profile) and the total incoming count rate at the detector.

Another example of these further signal component types is the aging peak. Aging peaks appear in measured pulse height spectra which are obtained by using an aged detector (in particular when using a gas detector with an aged wire). To account for aging peaks, in one embodiment, the model generator may further add one or more aging profiles to the PHSM if the detector used by the spectrometer is a gas detector. Aging profiles are generated by copying and shifting the respective diffraction order profile ensembles by a calibrated energy offset. That is, each diffraction order profile ensemble is copied and shifted by an energy offset derived from a respective calibrated aging model resulting in a respective aging profile ensemble. In the adjustment step (i.e., during the pulse height spectrum fitting), the model adjustment module scales the intensities of the generated diffraction order profile ensembles in relation to the intensities of the respective aging profile ensembles. In other words, during the fitting, aging ratios describing the relation between the intensities of diffraction order profile ensembles and their respective aging profile ensembles are used as fitting parameters.

Another signal component type is the so-called shelf contribution. In one embodiment, the model generator may add to one or more generated profiles of the PHSM corresponding one or more shelf contribution profiles as constant intensity values starting at the respective generated profile position and extending to a defined lower energy which depends on the detector type. For example, for a gas detector this defined lower energy is zero. The constant intensity values are determined by using a calibrated shelf intensity model reflecting dependencies of the intensity on respective energy positions. In other words, the model generator retrieves a constant intensity value for a respective generated profile by using the calibrated shelf intensity model and adds this constant value as an offset to the PHSM starting at the defined lower energy (e.g., zero energy) up to the energy position of the maximum of the respective profile.

It is to be noted that the herein disclosed approach further allows to provide the contribution area of any higher diffraction order profile ensemble. In particular, the contribution area of the second order profile ensemble can be used for improving the resolution of a goniometer measurement performed by the wavelength-dispersive X-ray fluorescence spectrometer as described in detail in the detailed description.

Performing a pulse height spectrum fitting as described with the adjusting step, the computer system can also ensure a removal of artifact contributions of different elements in a goniometer measurement performed by the spectrometer. Further, the herein described approach allows to reduce the influence of Bremsstrahlung background from higher orders of the pulse height spectrum. These effects are also described in more detail in the detailed description.

In one embodiment, a computer program product has computer readable instructions that, when being loaded into a memory of the computer system and being executed by one or more processors of the computer system allow the computers system to execute, at runtime, the herein described method steps for measuring peak intensities in pulse height spectra obtained by wave-length dispersive x-ray fluorescence spectrometers. In other words, the computer program product, when loaded into the computer system, implements the various functional modules of the computer system as described herein.

Further aspects of the description will be realized and attained by means of the elements and combinations particularly depicted in the appended claims. It is to be understood that both, the foregoing general description and the following detailed description are exemplary and explanatory only and are not restrictive.

DETAILED DESCRIPTION

Figure 1:
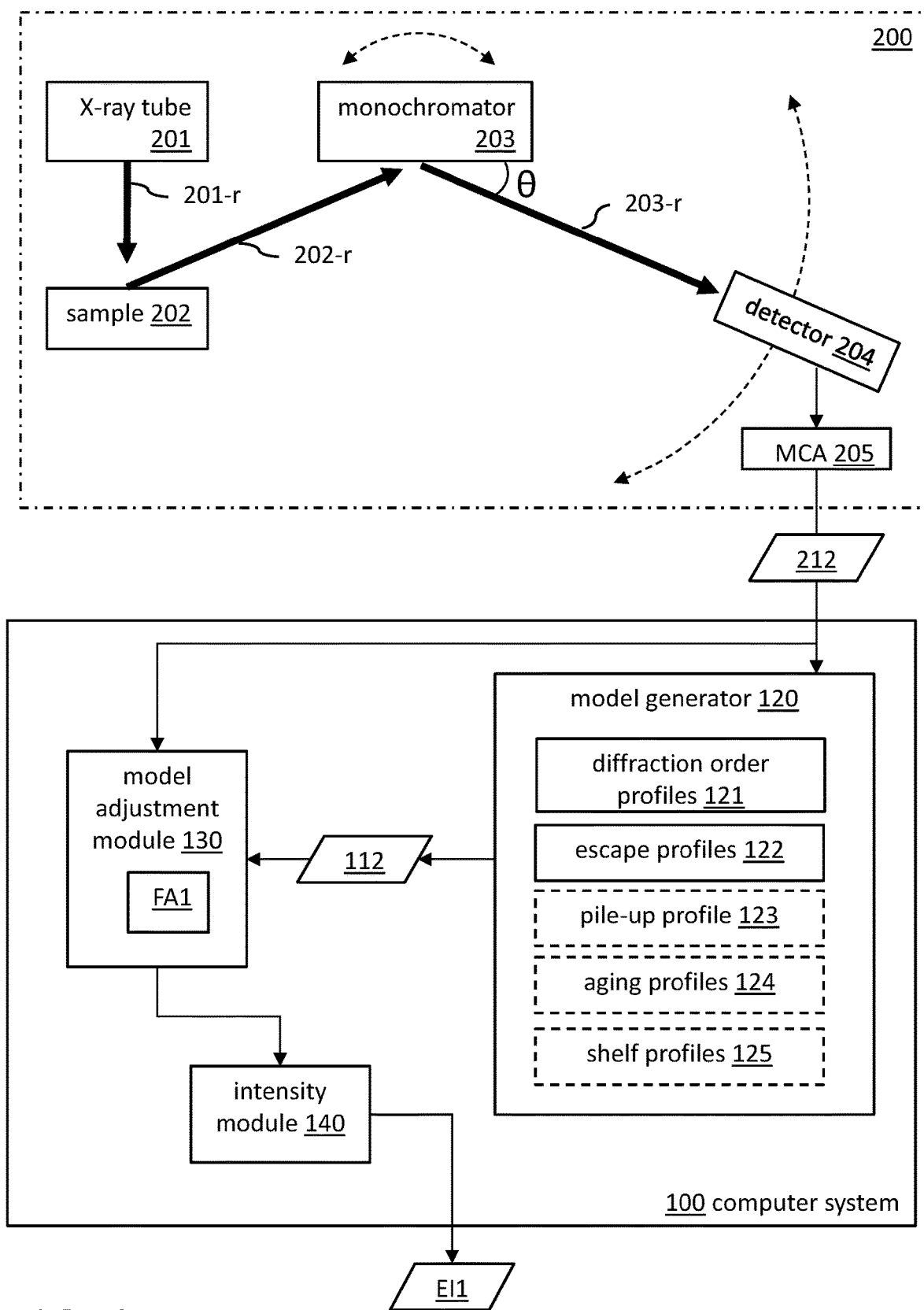
FIG. 1 includes a block diagram of an example embodiment of a computer system for measurement of peak intensities in pulse height spectra obtained by wave-length dispersive X-ray fluorescence spectrometers.
Figure 2:
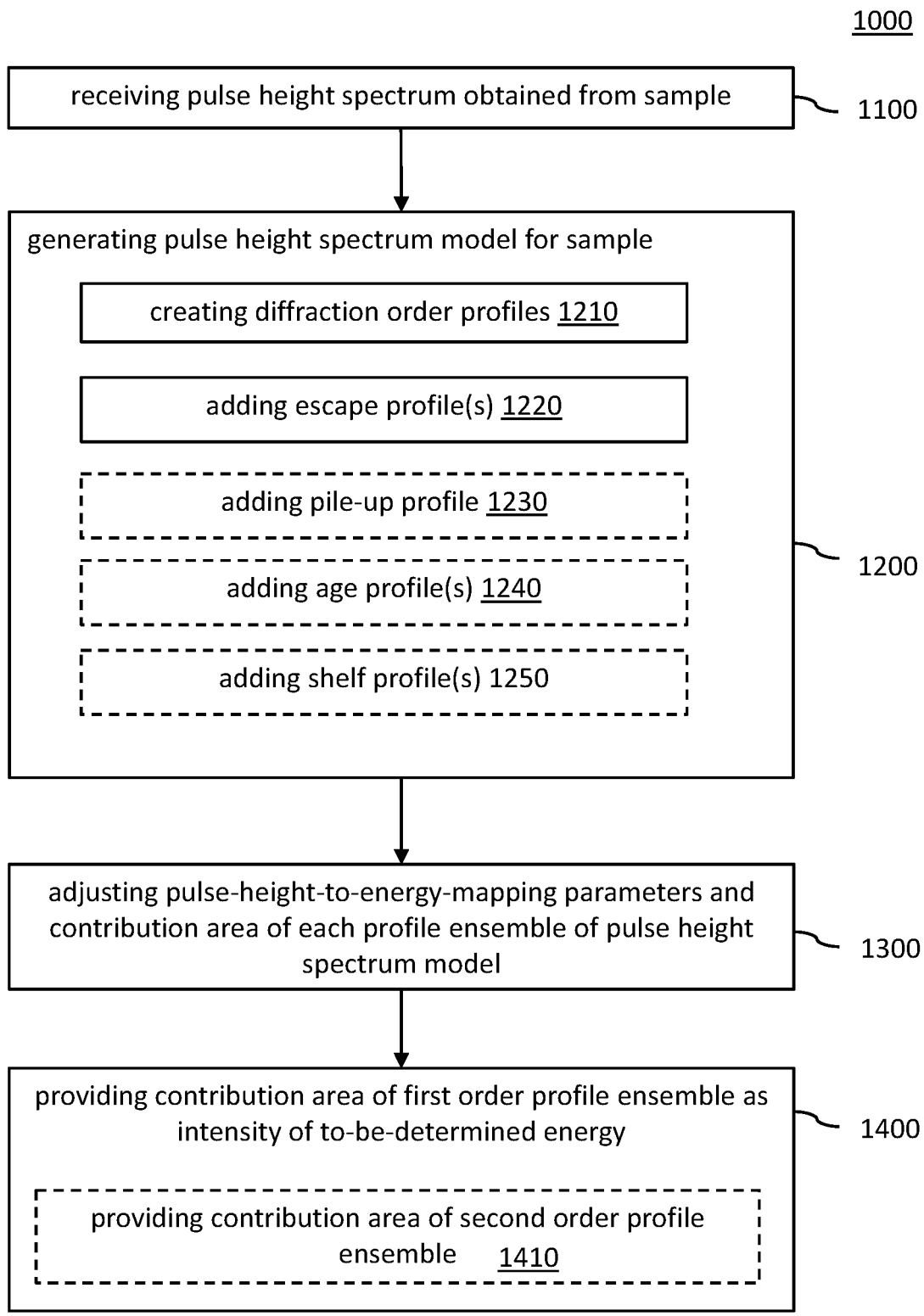
FIG. 2 is a simplified flow chart of a computer-implemented method for measurement of peak intensities in pulse height spectra obtained by wave-length dispersive X-ray fluorescence spectrometers according to an embodiment.

FIG. 1 includes a block diagram of an example embodiment of a computer system 100 for measurement of peak intensities in pulse height spectra obtained by a wave-length dispersive X-ray fluorescence spectrometer 200. The system 100 of FIG. 1 is described in the context of the simplified flow chart of a computer-implemented method 1000 for measurement of peak intensities in pulse height spectra as illustrated in FIG. 2. Therefore, the following description refers to reference numbers used in FIG. 1 and FIG. 2. The system 100 is thereby configured to execute the method 1000 when loading a respective computer program into a memory of the system and executing said program with processing means of the system. Said computer program product implements the functional modules 120, 130, 140 of system 100.

In the example embodiment of FIG. 1, the system 100 is communicatively coupled with the spectrometer 200. In an alternative embodiment, the computer system 100 may be an integrated component of the wave-length dispersive x-ray fluorescence spectrometer 200. In both embodiments, system 100 can receive 1100 pulse height spectrum 212 obtained by MCA 205 of the spectrometer 200 via an appropriate interface (not shown). The functioning of the spectrometer 200 has been described to a large extent in the background section. In general, a person skilled in the art knows how the spectrometer 200 can obtain the pulse height spectrum 212 from sample 202. Nevertheless, the functioning is briefly summarized in the following with a reference to FIG. 1.

The x-ray tube 201 generates polychromatic radiation 201-$r$ including characteristic lines and Bremsstrahlung which is directed on a sample 202 to be analyzed. This radiation generates polychromatic x-ray fluorescence and scattered radiation 202-$r$ in the sample 202. The radiation 202-$r$ emitted by the sample 202 is analyzed by measuring, with a goniometer, the radiation reflected by the monochromator 203 of the spectrometer at various diffraction angles θ. This technique is based on Bragg's law. X-ray photons 203-$r$ of multiples of the energy of the analytical signal arrive at the detector 204 of the spectrometer. A photon hitting the detector 204 is converted into an electric pulse where the pulse height is proportional to the energy of the photon. The multi-channel analyzer 205 (MCA) can then count the number of photons at energies corresponding to the various channels of the MCA resulting in the pulse height spectrum 212. Additional effects which may contribute to the pulse height spectrum have been described in the background section and will be described in more detail in the context of the figures and the respective detailed description. The herein disclosed approach is depicted with diffraction angle scans, but also applies to fixed diffraction angle measurements.

The system has a model generator 120 adapted to generate a pulse height spectrum model (PHSM) 112. The PHSM 112 is a model which is based on the various signal components which—in a measured pulse height spectrum—add up to the measured curve. As mentioned earlier, a pulse height spectrum typically includes at least diffraction order peaks and escape peaks. Therefore, the model generator 120 generates a PHSM which includes at least corresponding diffraction order profiles 121 and escape profiles 122. In optional embodiments of the model generator may further generate a pile-up profile 123 for the first order diffraction profile, aging profiles 124, and/or shelf profile 125.

A plurality of diffraction order profiles 121 is created 1210 with predefined profile shapes at photon energy positions corresponding to respective diffraction orders of the monochromator 203. The widths of the diffraction profiles are determined by using a calibrated width model reflecting dependencies of the widths on respective energy positions and total incoming count rate of the detector 204 of the spectrometer. The width model to be used can depend on the type of the detector. In the following, three example width models are shown. However, a person skilled in the art may also use other models for width determination of the diffraction profiles.

With E as energy and r as total incoming count rate, the profile width for the various detectors can be determined with the width models described by the mathematical terms T1 to T3 (other terms may be used, too, by a person skilled in the art):

S6 JAGUAR Counter:

$$\sqrt{0.01 \cdot E^2 + 0.08 \cdot E + 0.04} + 0.6 \cdot 10^{-6} r \quad \text{(T1)}$$

S8 TIGER Flow Counter:

$$\sqrt{0.01 \cdot E^2 + 0.08 \cdot E + 0.04} + 0.6 \cdot 10^{-6} r \quad \text{(T2)}$$

S8 TIGER Scintillation Counter:

$$0.46E+2.4 \quad \text{(T3)}$$

A generalization for the profile width is described by the model F3:

$$\sqrt{w_1 E^2 + w_2 E + w_3} + w_4 r \quad \text{(F3)}$$

with $w_1$, $w_2$, $w_3$ and $w_4$ as the calibration parameters for the profile width model F3.

The positions of the diffraction order profiles are then determined by their respective energies and a pulse-height-to-energy-mapping.

If a created diffraction order peak has a photon energy that is higher than the edge energy of the detector material of the detector, typically an escape peak is generated through the detector material. The model generator takes this into account by adding 1220 to the PHSM 112 a respective escape profile at the position of the photon energy of the diffraction order profile diminished by the fluorescence energy of the photon escaped from the detector material. Thereby, the intensity of the escape profile is determined by using a calibrated escape intensity model reflecting dependencies of the intensity on respective energy positions. In case of using a gas detector, the escape intensity model may also reflect a dependency on the gas pressure of the detector. The escape intensity model again depends on the detector type. Some examples of an escape intensity ratio (i.e., the ratio between the intensity of an escape profile and the intensity of its associated diffraction order profile) at sea-level pressure which can be used by the various detector types are (other appropriate values may be used instead dependent on the respective individual detector):

S6 JAGUAR Flow Counter: 0.075
S8 TIGER Flow Counter: 0.075
S8 TIGER Scintillation Counter: 0 (i.e., no escape profiles for this detector type)

A generalization for the escape intensity model is given by F4:

$$(e_1 E + e_2)(e_3 p + e_4) \quad \text{(F4)}$$

where $e_1$, $e_2$, $e_3$ and $e_4$ are the calibration parameters for the escape intensity ratio. p is the pressure of the gas in the gas detector. For non-gas detectors $e_3=0$ and $e_4=1$.

A model adjustment module 130 of system 100 uses a fitting algorithm FA1 to adjust 1300 the pulse-height-to-energy-mapping parameters (slope and offset) and the contribution area of each diffraction order profile ensemble of the pulse height spectrum model. The fitting algorithm FA1 is adapted to minimize the difference between the pulse height spectrum model 212 and the received pulse height spectrum 112. For example, a least-squares fitting algorithm may be used. Alternative fitting algorithms (e.g., method of minimum sum) may be used instead.

In general, fitting iteratively tries to find the minimal deviation between the model (PHSM) and the observation (measured pulse height spectrum). However, if the model depends non-linearly on the parameters to fit, there may be several local minima. Some fitting algorithms may converge in a local minimum, not finding the global minimum. Additionally, they may tend to overshoot in the first iterations leaving the path towards the global minimum. Fitting algorithms that find the global minimum are typically slow. in one embodiment, these issues can be mitigated by choosing starting values for the fitting parameters that are already close to the global minimum and by allowing the adjustment module 130 to only search in a sensible solution space. A sensible solution space as used herein means that there are no substantial deviations from previous determinations of pulse-height-to-energy mapping parameters. The starting values for the intensities of the diffraction order profile ensembles can be obtained by integrating the pulse height spectrum between 50-150% of (i.e., between 0.5 to 1.5 times) the respective diffraction order energy for the first order, 150-250% for the second order, and so on. A further limitation for only using positive intensities may also be used.

In other words, the fitting may use limitations for the fitting parameters with regard to diffraction order and escape profiles such as:
  box-constraints for the pulse-height-to-energy-mapping parameters to allow only small changes
  non-negative constraints for the contribution areas of the diffraction order profile ensembles.
Box-constraints are lower and upper boundary inequality constraints to restrict a parameter to be fitted in a predetermined range. Non-negative constraints are lower boundary inequality constraints with the lower boundary being zero. With regard to aging profiles (explained in more detail in FIG. 8), a box-constraint may be set for the aging ratio (i.e., the ratio between the intensity of an aging profile ensemble and the intensity of its associated diffraction order profile ensemble) to remain between 0 and 1.

An intensity module 140 of system 100 finally provides 1400 the contribution area of the first order profile ensemble as the intensity Ell of the energy to be determined by the wavelength-dispersive X-ray fluorescence spectrometer 200. Because the PHSM automatically knows the contribution of each signal model component, after fitting, the contribution area of the first order profile ensemble is immediately known from the fitted PHSM 112 because each of the profiles of the PHSM represents an integrable function.

Figure 3:
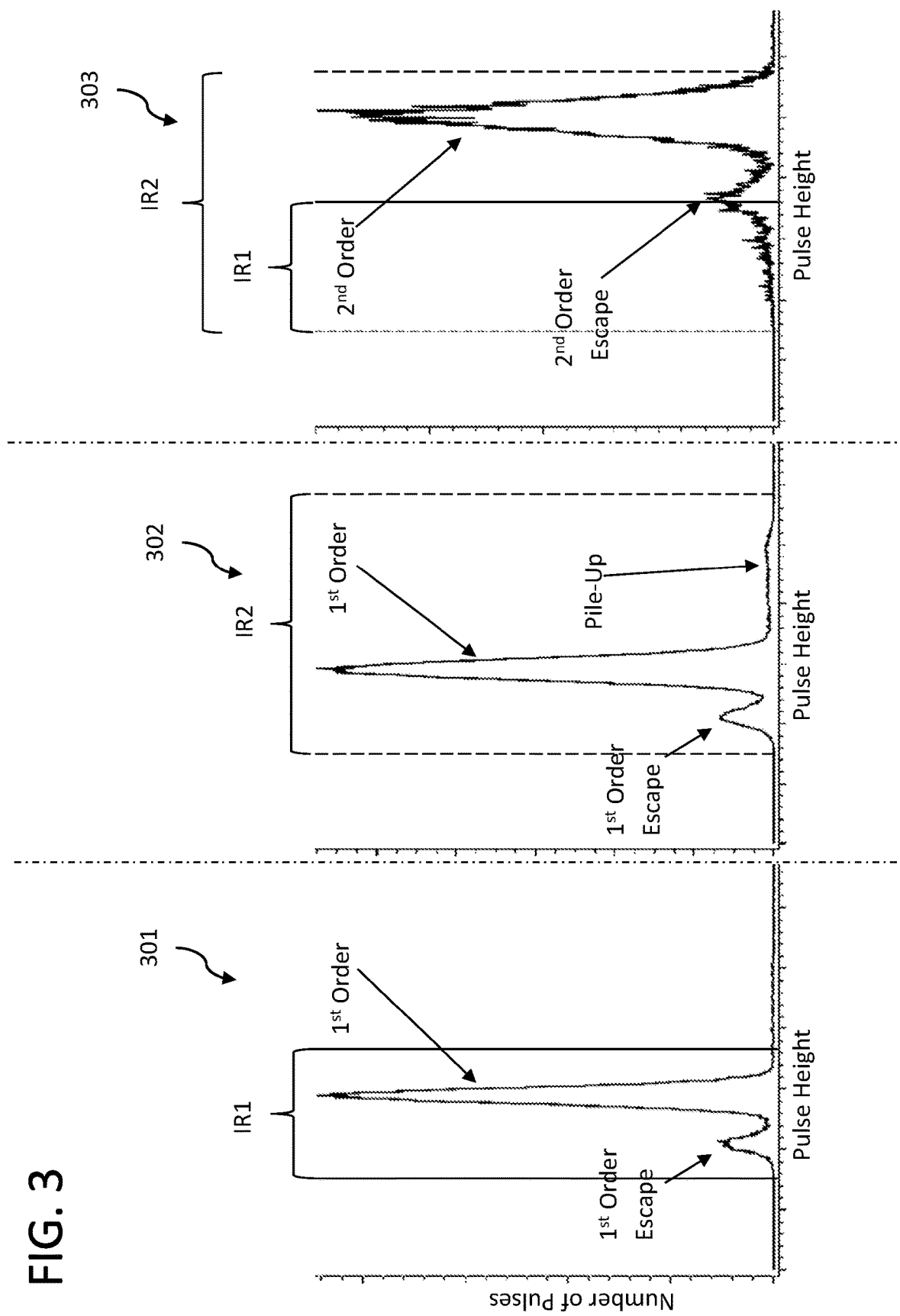
FIG. 3 illustrates overlapping signal contributions from different diffraction orders in a measured pulse height spectrum for respective integration regions.

FIG. 3 illustrates the problem of overlapping signal components from different diffraction orders in real measured pulse height spectra. In graph 301, a pulse height spectrum of a $1^{st}$ order peak associated with a $1^{st}$ order escape peak is shown. To determine the intensity of the analytical signal— in this example of a low intensity $1^{st}$ order peak, traditionally a narrow fixed integration range (interval IR1) was used, suitable to include both the contribution of the $1^{st}$ order peak and the contribution of its escape peak. Graph 302 illustrates a $1^{st}$ order peak with a high intensity where, in addition, a pile-up is observed. In traditional peak evaluation methods, a wider fixed integration range IR2 may be used to also capture the contribution of the pile-up to the first order intensity. Graph 303 illustrates how signal contributions of the $2^{nd}$ order now overlap with the fixed integration ranges IR1, IR2 in both scenarios (low intensity graph 301 and high intensity graph 302). The $2^{nd}$ order escape peak overlaps with the narrow fixed integration range IR1. With regard to the wider fixed integration range IR2, the $2^{nd}$ order escape peak and the $2^{nd}$ order peak entirely overlap with the integration range IR2. That is, the to-be-determined intensity of the analytical signal ($1^{st}$ order contributions) is distorted by higher order signal contributions in the fixed integration ranges. This typically leads to inaccurate measurements when using fixed integration ranges.

Figure 4:
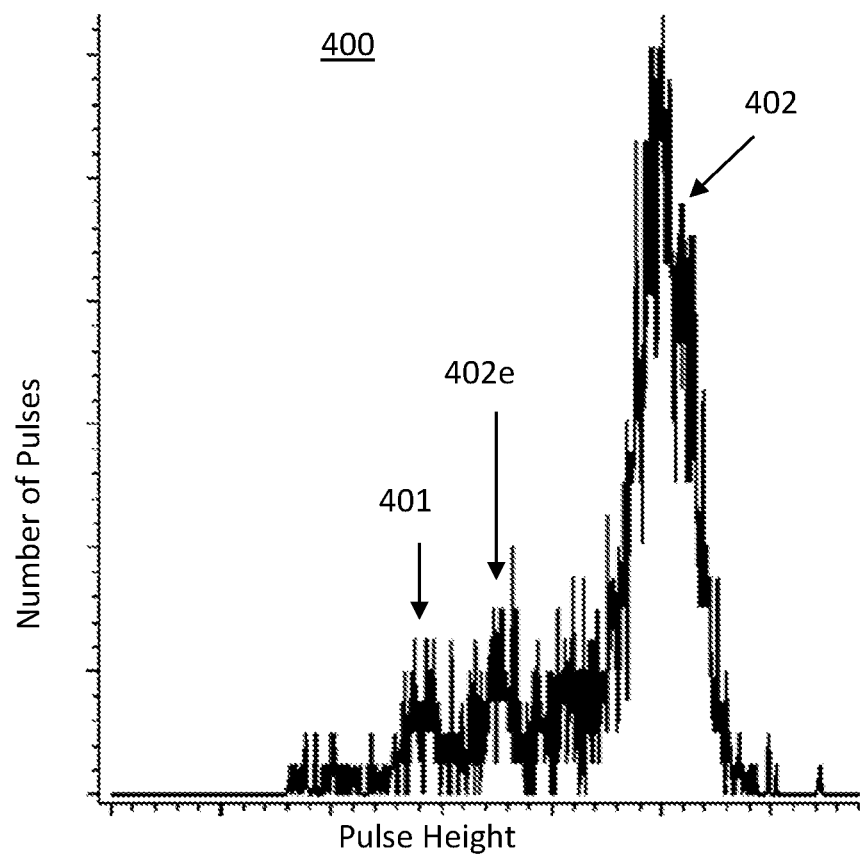
FIG. 4 illustrates contributions of different signal types for a particular diffraction order in a measured pulse height spectrum.

FIG. 4 illustrates a further example of a pulse height spectrum 400 with a $1^{st}$ order peak 401, a $2^{nd}$ order peak 402, and a $2^{nd}$ order escape peak 402e. In this example, the escape peak 402e (originating from the $2^{nd}$ order peak 402) overlaps with the analytical signal 401. In such cases, no integration range can be found at all that excludes such interference of higher diffraction orders with the analytical signal. It is to be noted that overlaps with the analytical signal can even originate from diffraction orders higher than 2. For example, for an aluminum Al KA1 fluorescence line from the sample, the $1^{st}$ order peak is at approximately at 1.5 keV. The $2^{nd}$ order peak is at 3 keV (which is less than the edge energy of 3.3 keV of the detector material argon (Ar)→no escape peak). The $3^{rd}$ order peak is at 4.5 keV (corresponding to a titanium Ti KA1 fluorescence line) which creates an escape peak at 1.5 keV (4.5 keV diminished by the Ar KA1 fluorescence energy of 3 keV), thus overlapping with the $1^{st}$ order analytical signal. Further, as mentioned above, peak positions may change with the signal intensity, temperature, and the age of the detector leading to additional types of potentially overlapping signal contributions.

Figure 5:
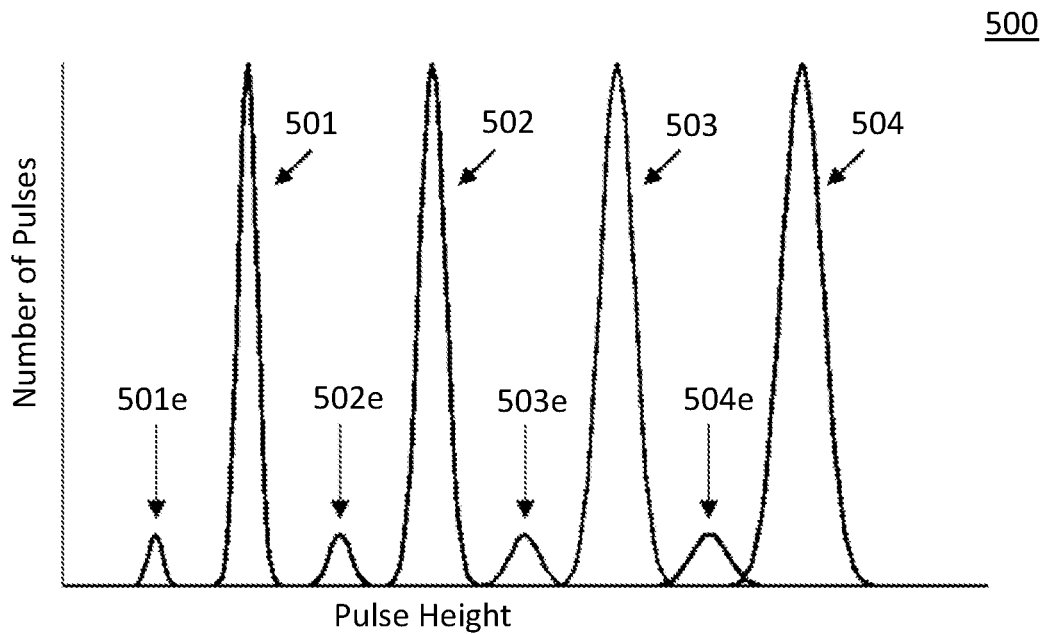
FIG. 5 illustrates a generated pulse height spectrum model with diffraction order profiles and escape profiles.

FIG. 5 illustrates a generated PHSM 500 with diffraction order profiles 501 to 504 and escape profiles 501e to 504e. The example model 500 uses Gaussian shaped profiles at the position of the photon energies corresponding to the diffraction orders of the monochromator. The highest visible diffraction order depends on the energy range of the detector and on the expected interferences (overlaps), which are detector specific. In the example, for each diffraction order profile an escape profile is added. However, generating the PHSM, escape profiles are only added to a respective diffraction order profile ensemble if the corresponding photon energy is higher than the edge energy of the detector material. For the example model 500 it is assumed that this is the case for all diffraction order profile ensembles.

The escape intensity ratio (ratio between intensity of escape profile and intensity of associated diffraction order profile) is determined by the escape intensity model described above which takes into account the energy and the detector material. The profile width increases with the energy of the respective profile in accordance with a calibrated width model as disclosed previously. The relative positions of the profiles are determined by their respective energies and a pulse-height-to-energy-mapping. A PHSM that comprises diffraction order profiles and escape profiles is considered to be a basic embodiment. However, it is to be emphasized again that not each diffraction order profile ensemble needs to include both profile types. In some cases, escape profiles are only included in diffraction order profiles of higher orders.

Figure 6:
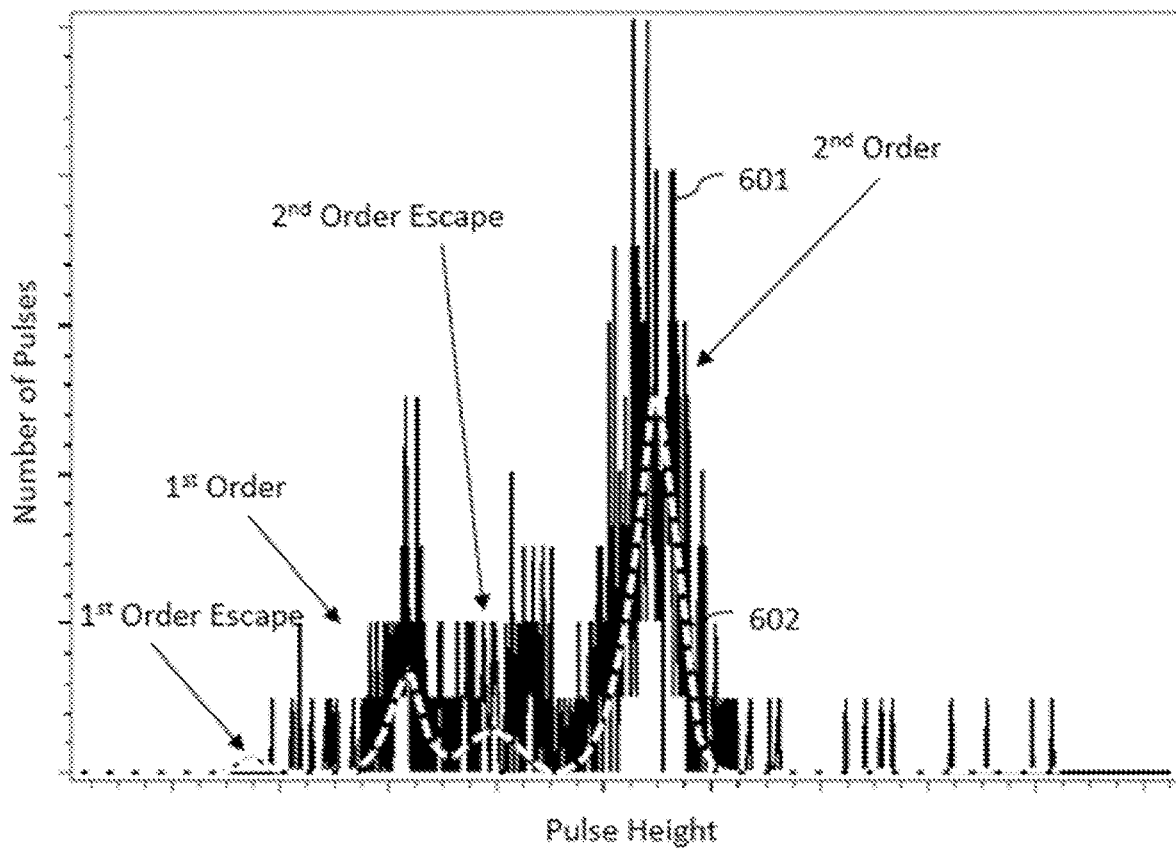
FIG. 6 shows a measured pulse height spectrum and pulse height spectrum model with diffraction order and escape profiles after fitting according to an embodiment.

FIG. 6 shows a measured pulse height spectrum 601 and a pulse height spectrum model 602 (white dashed line) with diffraction order and escape profiles after fitting. In the example, the pulse height spectrum 601 has a $1^{st}$ order peak, a 1st order escape peak, a $2^{nd}$ order peak and a $2^{nd}$ order escape peak which partially overlaps with the $1^{st}$ order peak. The fitted model 602 has been adjusted by using the pulse-height-to-energy-mapping parameters slope and offset and the contribution areas of the $1^{st}$ order profile ensemble (including the $1^{st}$ order diffraction profile and the 1st order escape profile) and the $2^{nd}$ order profile ensemble (including the $2^{nd}$ order diffraction profile and the $2^{nd}$ order escape profile) to minimize the difference between the spectrum 601 and the PHSM 602.

When generating the PHSM, profiles of further profile types may be added to the spectrum before the fitting. In one embodiment, the model generator 120 may add 1230 a pile-up profile to the first order diffraction profile. The intensity of the pile-up is determined by using a calibrated pile-up intensity model. Also, the pile-up intensity ratio depends on the detector type. The pile-up intensity ratio is the ratio between intensity of the pile-up profile and the intensity of the first order diffraction profile.

With r as the total count rate, the following detector dependent pile-up intensity ratios may be used when adding a pile-up profile:

S6 JAGUAR Flow Counter:

$$1.4 \cdot 10^{-13} r + 4.5 \cdot 10^{-8} + 1.2 \cdot 10^{-5}/r \tag{T4}$$

S8 TIGER Flow Counter:

$$1.4 \cdot 10^{-13} r + 4.5 \cdot 10^{-8} + 1.2 \cdot 10^{-5}/r \tag{T5}$$

S8 TIGER Scintillation Counter:

$$3.5 \cdot 10^{-16} r + 3 \cdot 10^{-9} + 5.8 \cdot 10^{-2}/r \tag{T6}$$

A generalization for the pile-up intensity model is described by F5:

$$p_1 r + p_2 + p_3/r \tag{F5}$$

where $p_1$, $p_2$ and $p_3$ are the calibration parameters for the pile-up intensity ratio.

Figure 7:
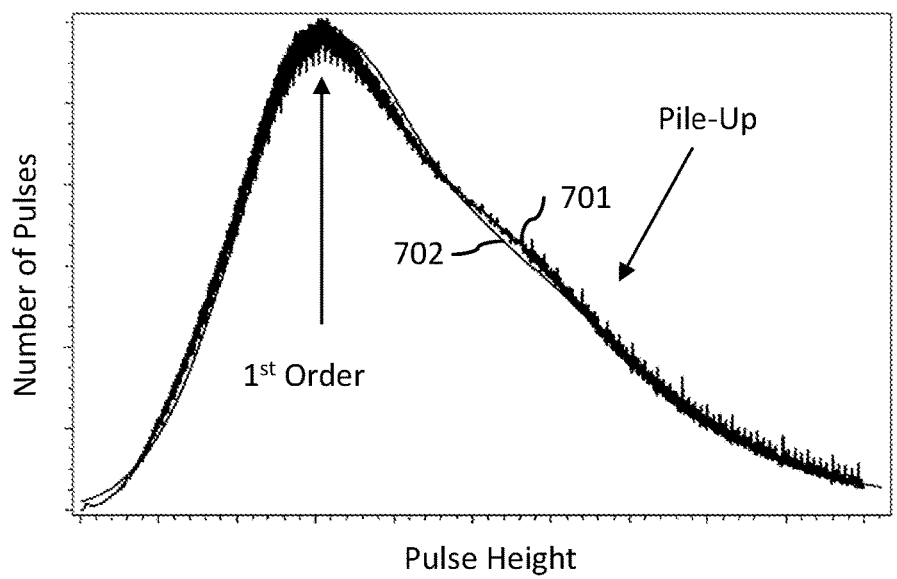
FIG. 7 shows a first order peak of a measured pulse height spectrum with a pile-up and a corresponding fitted first order profile ensemble according to an embodiment.

FIG. 7 shows an example of a $1^{st}$ order peak in a measured pulse height spectrum 701 which shows a pile-up on the declining edge of the peak. Curve 702 represents the fitted PHSM which includes a pile-up profile in the $1^{st}$ order profile ensemble. Since pile-up is generated by two photons from the analytical signal, the intensity of the analytical signal is not just the sum of the intensities of the main peak and the pile-up. It is rather the sum of the main peak intensity and double the intensity of the pile-up. A fixed integration range method could only give the uncorrected sum when choosing a wide integration range. This causes a non-linear response of the detector to increasing intensities. The non-linearity grows as the pile-up increases with increasing intensity and the error of the summation gets larger and larger. The herein disclosed pulse height spectrum fitting approach uses separate profiles for the $1^{st}$ order diffraction profile and the pile-up profile so that the pile-up and the $1^{st}$ order diffraction intensity are added up correctly. This increases the linearity of the detector up to significantly higher count rates.

Figure 8:
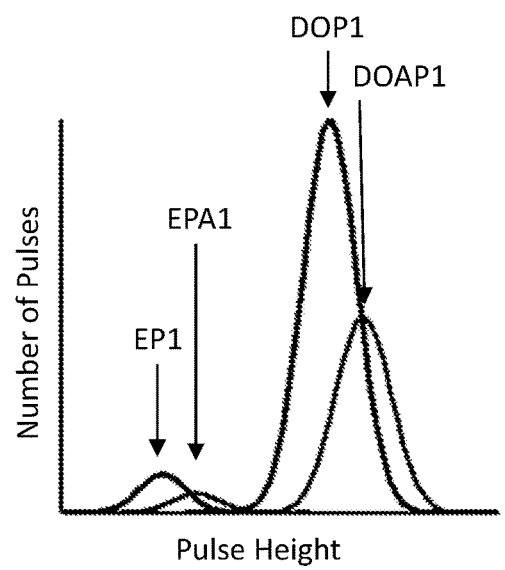
FIG. 8 illustrates generation/creation of an aging profile for a diffraction order profile ensemble according to an embodiment.

A further profile type which may be added by the model generator is for representing so-called aging peaks. Gas detectors show an aging effect due to wire aging. As a consequence, aging peaks are generated by an aged gas detector of the spectrometer for each peak in a pulse height spectrum. Therefore, in case of a gas detector being used by the spectrometer, the model generator adds 1240 one or more aging profiles to the pulse height spectrum model 112 to account for the aging effect. This is achieved by copying and shifting the generated diffraction order profile ensembles by a calibrated energy offset. FIG. 8 illustrates a diffraction order profile ensemble with a diffraction order profile DOP1 and an escape profile EP1. The model generator copies and shifts DOP1 and EP1 by the calibrated energy offset to higher energies. Then, the intensity of the diffraction order profile ensemble (DOP1, EP1) is scaled in relation to the intensities of the respective shifted profiles resulting in the shifted, rescaled aging profiles EPA1 and DOAP1. In other words, the relative intensity between the profiles of a diffraction order profile ensemble and the respective aging peaks are fitted while the offset between the original profiles and the shifted aging profiles are fixed. In other words, the ratios between the intensities of the shifted aging profile ensembles and the corresponding diffraction order profile ensembles are adjusted by the fitting algorithm whereas the shift is provided by a calibration.

Another type of profile which may be added 1250 to the PHSM 112 (cf. FIG. 1) is the so-called shelf. For this profile type, a constant contribution may be added to each generated profile extending from the respective profile position to a defined detector dependent lower energy defining the shelf for said profile. The constant intensity values are determined by using a calibrated shelf intensity model. The shelf intensity ratio (i.e., the ratio between the intensity of a shelf profile and the intensity of its associated diffraction order profile) again depends on the detector type and energy E. The following terms may be used:

S6 JAGUAR Flow Counter:

$$\begin{cases} 0, & E < 4.1 \text{ keV} \\ 9 \cdot 10^{-3} E - 3.7 \cdot 10^{-2}, & E \geq 4.1 \text{ keV} \end{cases} \quad (T7)$$

S8 TIGER Flow Counter:

$$\begin{cases} 0, & E < 4.1 \text{ keV} \\ 9 \cdot 10^{-3} E - 3.7 \cdot 10^{-2}, & E \geq 4.1 \text{ keV} \end{cases} \quad (T8)$$

S8 TIGER Scintillation Counter:

0 (no shelfs for this detector type)

Generalization for Shelf Intensity:

$$\begin{cases} 0, & E < s_1 \\ s_2 E + s_3, & E \geq s_1 \end{cases} \quad (F6)$$

where $s_1$, $s_2$ and $s_3$ are the calibration parameters for the shelf intensity ratio.

Figure 10A:
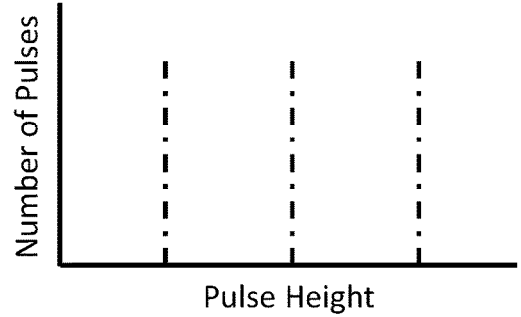
FIGS. 10A to 10D illustrate various steps towards the generation of an example of a pulse height spectrum model with diffraction order, escape and aging profiles according to an embodiment.
Figure 10B:
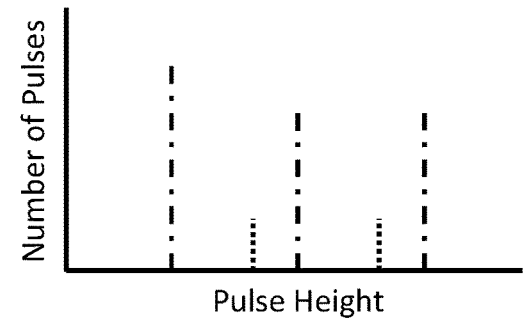
Figure 10C:
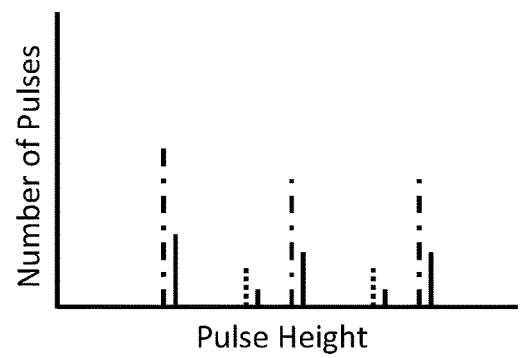
Figure 10D:
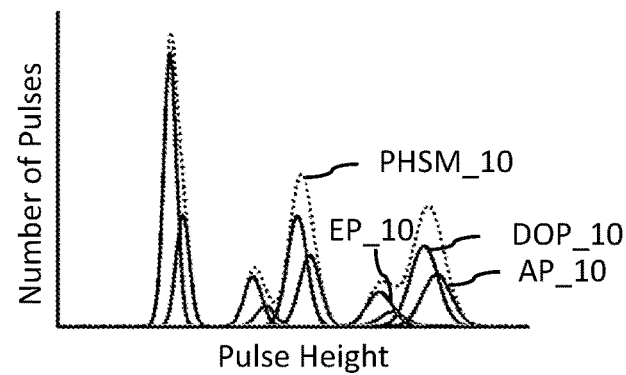

FIGS. 10A to 10D illustrate various steps towards the generation the generation of an example of a pulse height spectrum model with diffraction order, escape and aging profiles. In FIG. 10A, the dash-dotted lines represent the energy positions for the diffraction order profiles. In FIG. 10B, the energy positions of escape profiles for the higher diffraction orders are added and represented by the dotted lines. When adding an escape profile to a diffraction order profile, the intensity of the diffraction order profile is reduced by the intensity of the added escape profile so that the intensity of the respective diffraction order profile ensemble remains constant. In FIG. 10C, the energy positions of aging profiles are added for all diffraction order profile ensembles represented by solid lines. Finally, in FIG. 10D all lines are convoluted with a profile shape (e.g., Gaussian shape) rendering the respective diffraction order, escape and aging profiles (e.g., $2^{nd}$ order diffraction profile DOP_10, $2^{nd}$ order escape profile EP_10, and $2^{nd}$ order aging profile AP_10). The sum of all profiles results in the pulse height spectrum model PHSM_10 which is represented by the dotted line in FIG. 10D.

Figure 11:
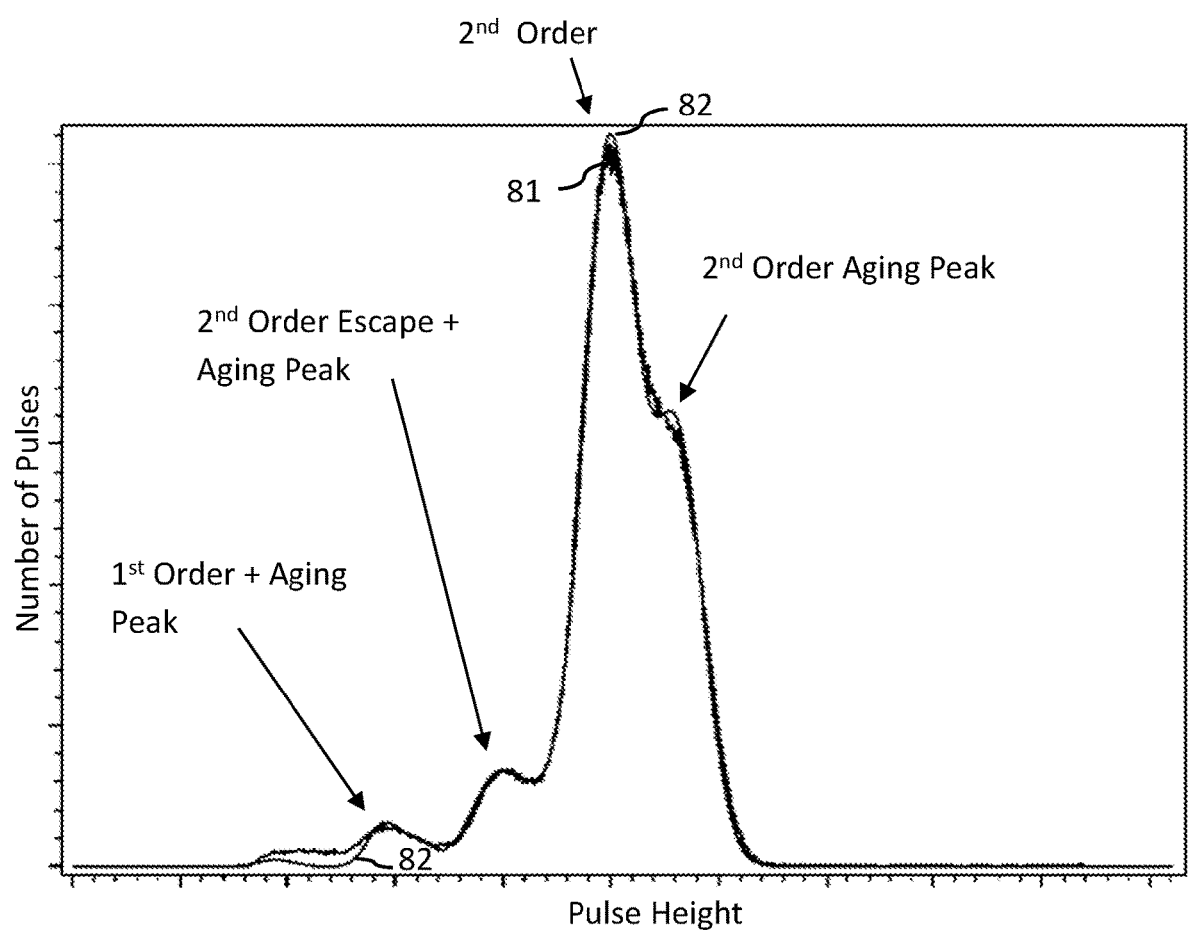
FIG. 11 shows a measured pulse height spectrum with a fitted pulse height spectrum model with diffraction order, escape and aging profiles according to an embodiment.

FIG. 11 shows a measured pulse height spectrum 81 with a fitted pulse height spectrum model 82. Spectrum 81 was obtained by using a flow counter gas detector where the charged particles generated by the incidence x-ray photon are collected by a wire in the center of the detector. Over time, the wire surface deteriorates (aging effect) leading to a change of the peak shapes in the measured pulse height spectrum. In this example, the $1^{st}$ order diffraction peak overlaps with aging peak of the $1^{st}$ order. Further, also the $2^{nd}$ order escape peak has an overlap with the $1^{st}$ order aging peak. The $2^{nd}$ order peak has a strong overlap with its own aging peak. The PHSM 82 has been created by creating respective diffraction order profiles, escape profiles and aging profiles and fitting the resulting diffraction order profile ensembles to the measured pulse height spectrum 81 using slope and offset of the pulse-height-to-energy mapping as well as the contribution areas of the respective profile ensembles and the aging peak ratio as fitting parameters. The fitted PHSM 82 comes very close to the original measured spectrum 81. Because PHSM 82 knows exactly the contribution area of the $1^{st}$ order diffraction profile ensemble and its corresponding aging profile ensemble, the intensity of the analytical signal can be accurately determined. In a classic approach using integration regions this would be impossible.

Figure 9A:
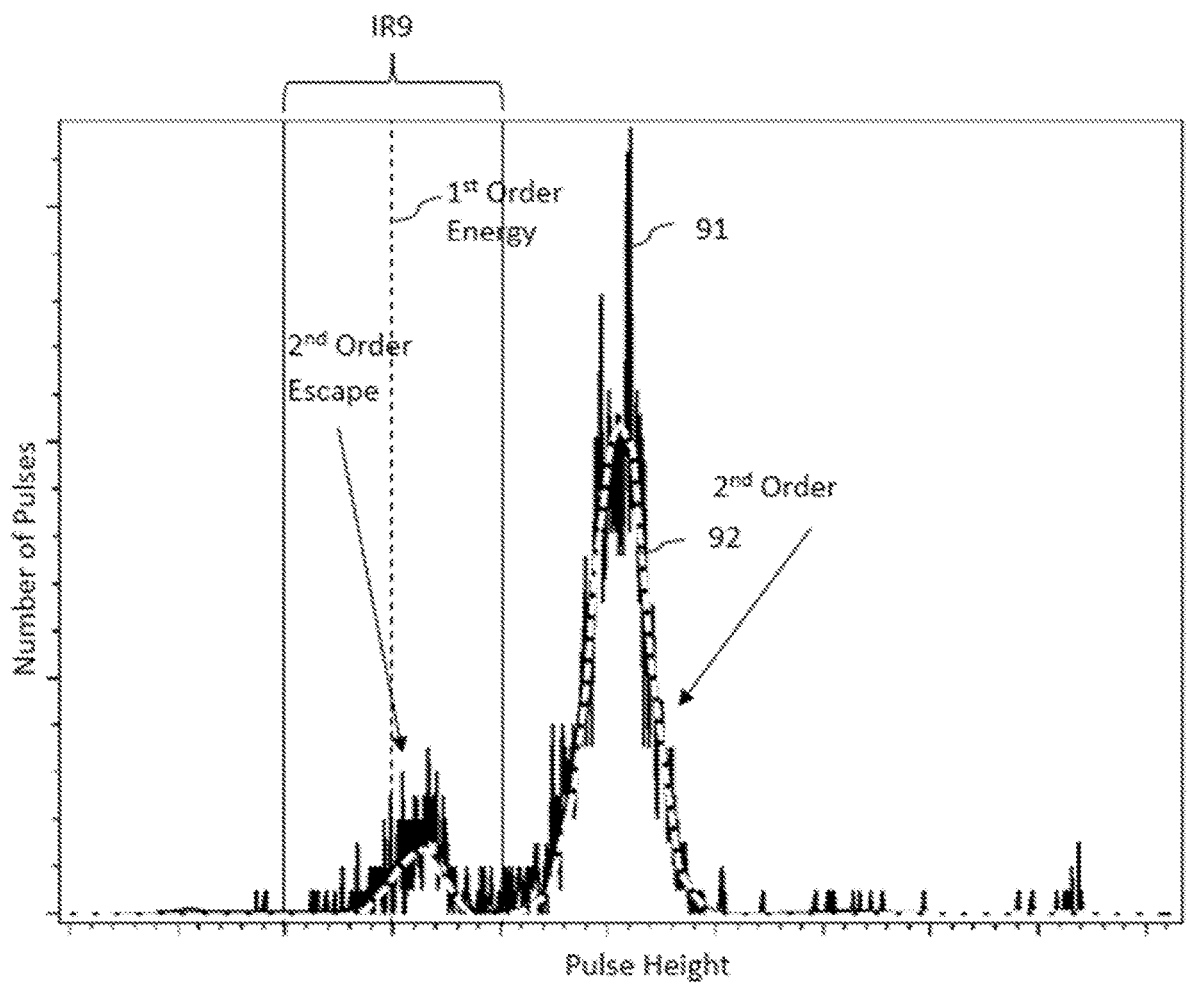
FIGS. 9A to 9C illustrate improvements gained when evaluating a measured pulse height spectrum using pulse height spectrum fitting according to an embodiment.
Figure 9B:
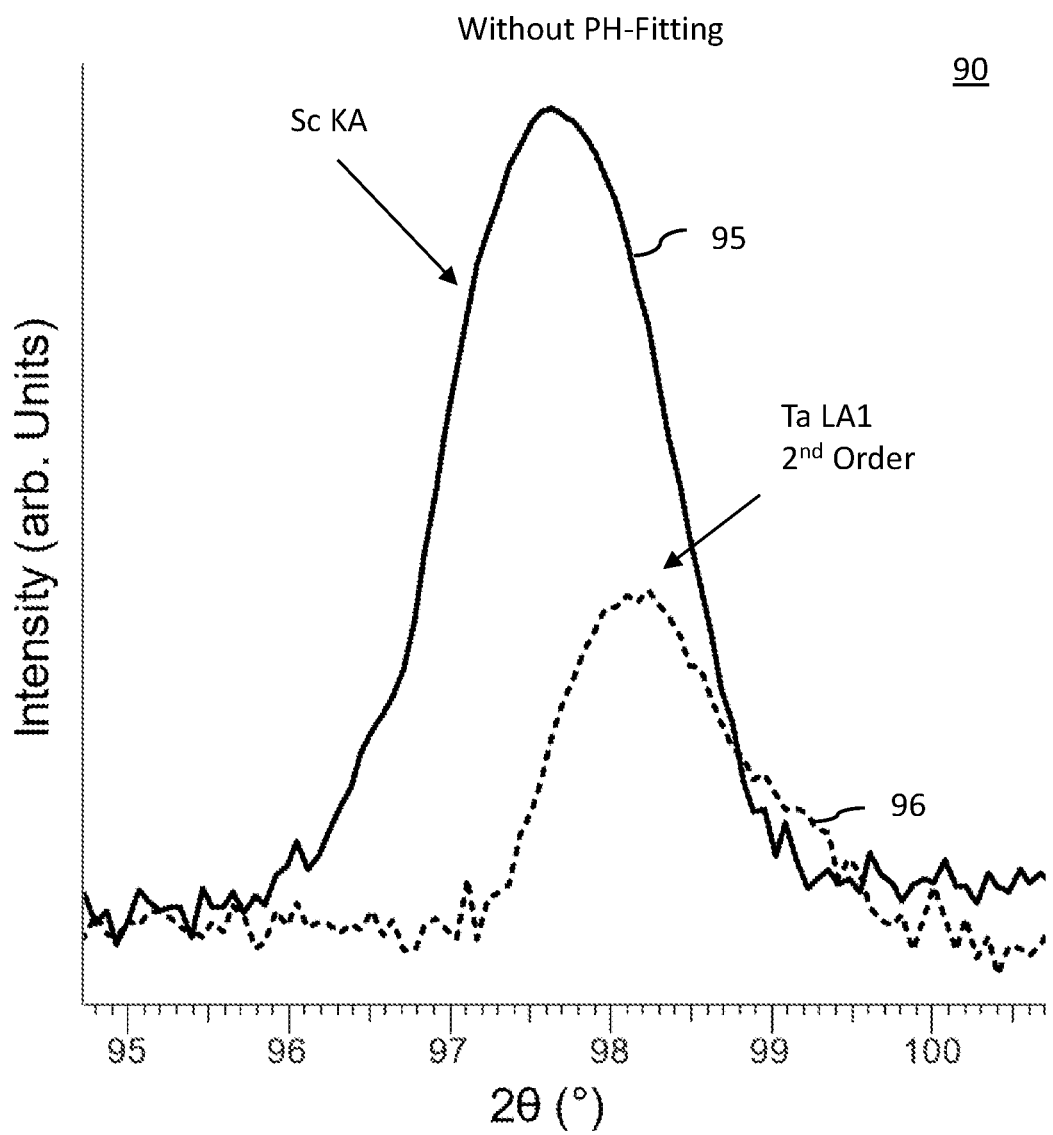
Figure 9C:
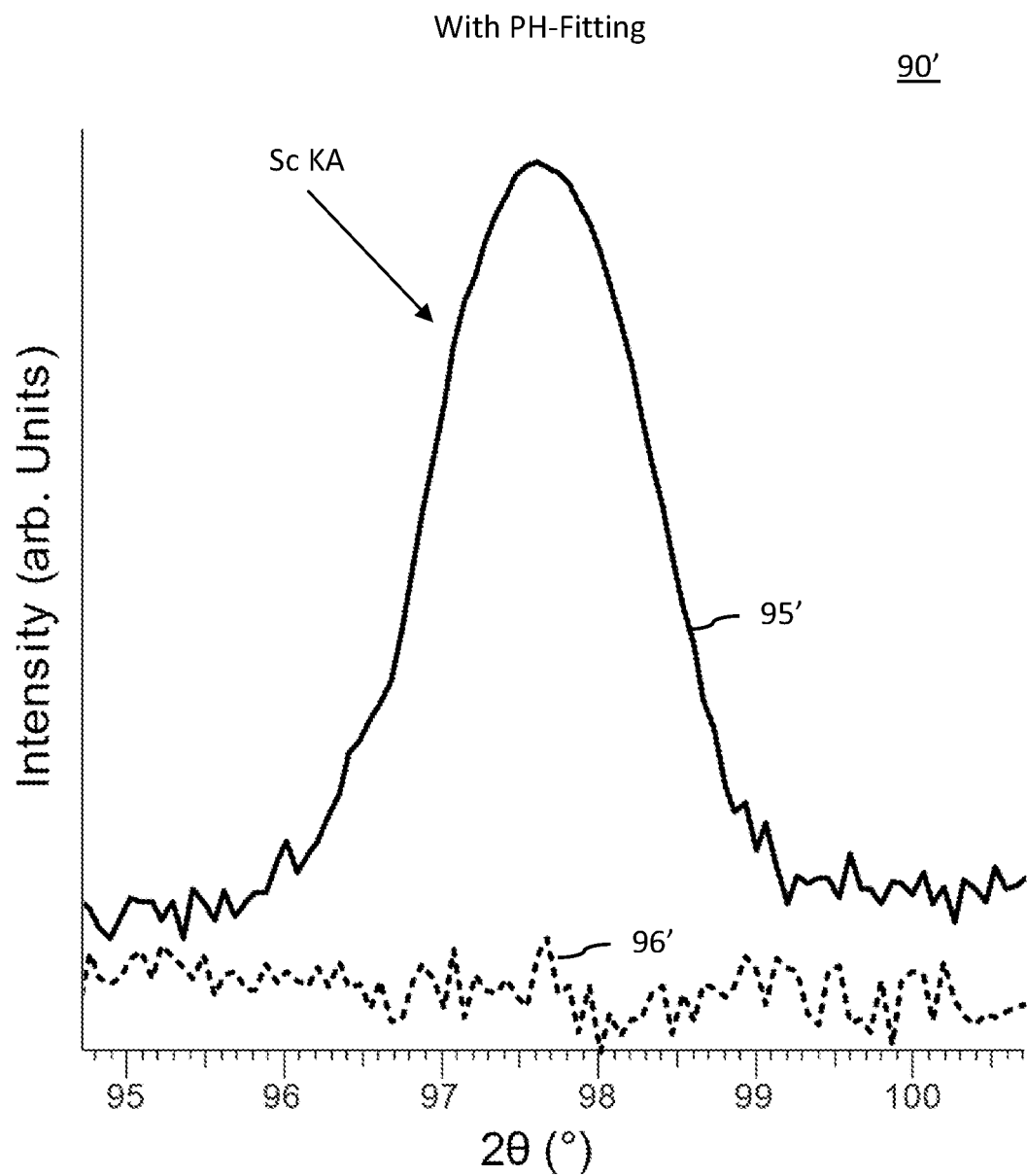

FIGS. 9A to 9C illustrate improvements gained when evaluating a measured pulse height spectrum using pulse height spectrum fitting according to an embodiment. FIG.

9A illustrates a measured pulse height spectrum 91 which is dominated by second diffraction order contribution and a fitted PHSM 92 (dashed white line). A fixed integration range IR9 is centered at the dashed vertical line indicating the energy of the analytical signal. The fixed integration range adds the $2^{nd}$ order escape peak to the integration result.

FIGS. 9B and 9C illustrate the same goniometer scan of two samples performed by the spectrometer where each point is the result of extracting the intensity from the pulse height spectrum with two different methods. In FIG. 9B, the analytical signal was extracted using classic integration within the integration range IR9. The spectrum 95 was measured using a sample that only contains scandium (Sc), while the spectrum 96 (dashed curve) was measured using a sample that only contains tantalum (Ta). As demonstrated in FIG. 9A the second order Ta LA1 intensity contributes to the integration range IR9 via the escape peak. This gives rise to artifacts in the form of a peak in the spectrum 96 while there should not be any signal, since no Sc is present in the sample. For a simplified visualization of graph 90, only samples containing either element are shown. Samples containing a mixture of both elements will show the sum of both peaks and thus Ta will hinder the quantification of Sc. When looking at graph 90' in FIG. 9C (extraction with pulse height spectrum fitting), only the peak for Sc KA (curve 95') is present in the spectrum of the sample containing Sc. No artifact peaks appear in the spectrum 96' of the sample only containing Ta because the influence of second order peaks is entirely eliminated when using the herein disclosed pulse height spectrum fitting approach. Since the spectrum from the sample also contains the scattered Bremsstrahlung from the tube, which is continuous over all energies, the higher order of the monochromator will always contribute intensity to the integration range IR9 when the escape peak of the higher order falls within the integration range. Thus, separating the influence of the higher order escape peak on the first order intensity using pulse height spectrum fitting reduces the contribution of the higher order Bremsstrahlung on the analytical signal significantly.

Figure 12:
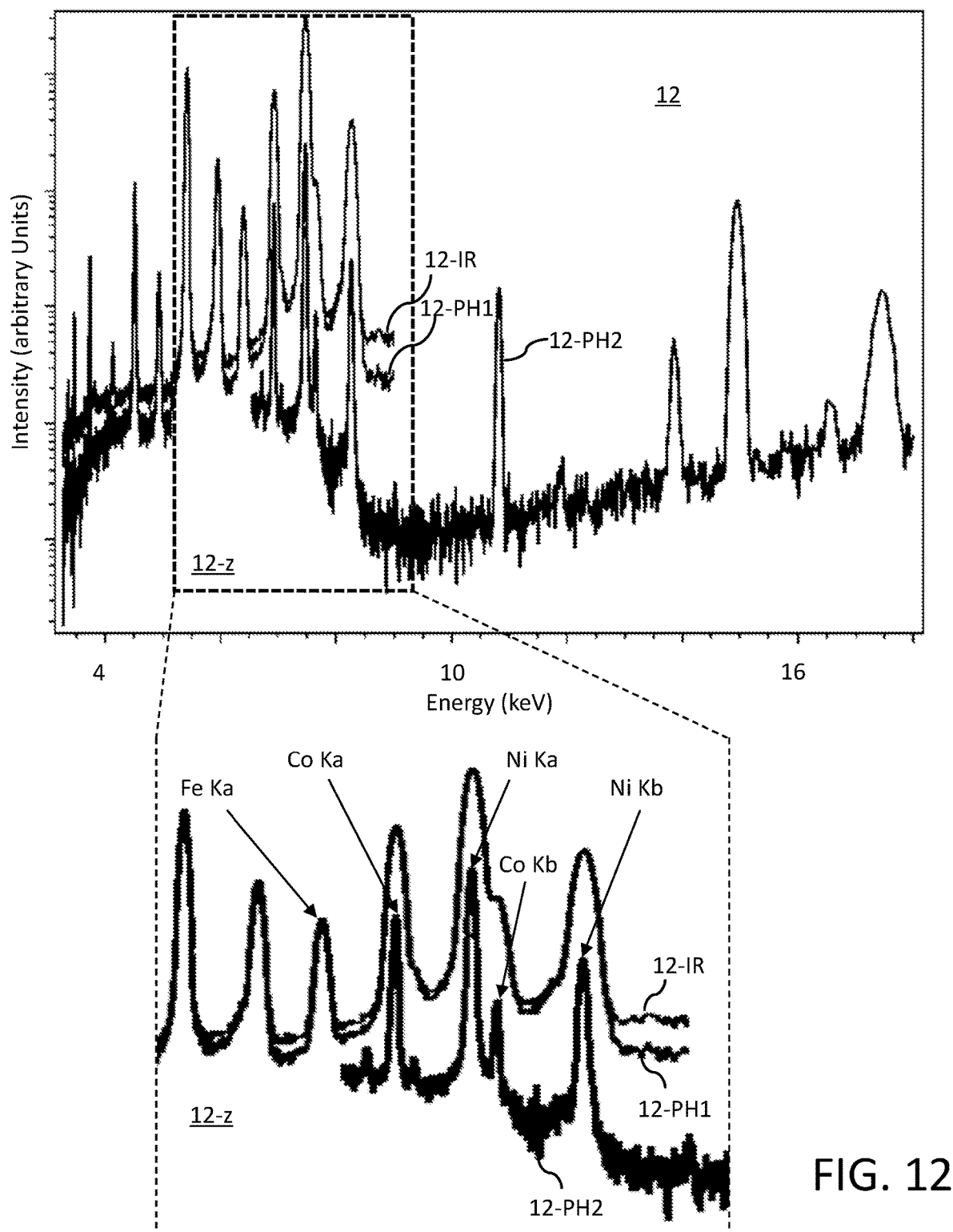
FIG. 12 illustrates improvement of the resolution of a goniometer measurement by providing second order profile intensities according to an embodiment.

In one embodiment, the intensity module 140 (cf. FIG. 1) is further adapted to provide 1410 (cf. FIG. 2) the contribution area of at least the second order profile ensemble for improving the resolution of a goniometer measurement performed by the wavelength-dispersive X-ray fluorescence spectrometer 200. The energy error of the second order profile ensemble is smaller than the energy error of the first order profile ensemble which is illustrated in FIG. 12. In other words, a resolution improvement of the spectrometer can be achieved when considering also considering higher orders—at least the second order.

A wave-length dispersive x-ray spectrometer is using a monochromator to select an energy E to analyze by adjusting the diffraction angle θ on the monochromator according to the Bragg Equation:

$$\frac{n\ 12.4\ \text{Å}\ \text{keV}}{E} = 2\ d\ \sin(\theta) \tag{F7}$$

where n is the diffraction order and d is the lattice plane distance. However, since the diffraction order can by any positive integer, the monochromator actually allows multiple energies to be reflected to the detector. The energy of the second order is two times the energy of the first order, the energy of the third order is three times the energy of the first order, and so on. Pulse height spectrum fitting not only provides the intensity of the first, but also the intensity of the higher orders simultaneously as the pulse height spectrum model includes all the respective separated diffraction order profile ensembles. First and higher orders are recorded at the same diffraction angle but correspond to different energies.

Consequently, the intensity of all orders can be plotted over energy as shown in the graph 12 of FIG. 12. Curve 12-IR represents the intensity obtained by the fixed integration window method. The curve 12-PH1 represents first order intensity obtained by using the pulse height spectrum fitting approach. Curve 12-PH2 represents the second order intensity obtained by using the pulse height spectrum fitting approach. The x-axis is energy in keV. The y-axis is the intensity in arbitrary units (logarithmic scale). It is clearly visible in graph 12-z that the 12-PH2 peaks associated with Co KA, Ni Ka, Co KB and Ni Kb are much narrower than the corresponding 12-PH1 peaks at the same position. However, the intensity is diminished by roughly a factor of ten.

The following describes the resolution improvement mathematically. Only typical diffraction angles $0°<\theta<90°$ are allowed. Measuring the same energy at different diffraction orders gives:

$$\frac{1*12.4\ \text{Å}\ \text{keV}}{E} = 2\ d\ \sin(\theta_1) \tag{F8}$$

for the first order, and $$\frac{2*12.4\ \text{Å}\ \text{keV}}{E} = 2\ d\ \sin(\theta_2) \tag{F9}$$

for the second order. This can be combined to give:

$$\sin(\theta_2) = 2\sin(\theta_1) \tag{F10}$$

Since sinus is monotonically increasing in the given θ range, $$\theta_2 > \theta_1. \tag{F11}$$

The broadening of the peaks is dominated by the angular resolution of the diffractometer (the crystal of the monochromator). The angular error $\Delta\theta$ can be expressed as energy error $\Delta E$ by error propagation:

$$\Delta E = E|\cot(\theta)|\Delta\theta. \tag{F12}$$

The energy error can be calculated for the first and second order measurement of the same energy at different diffraction angles $$\Delta E_1 = E|\cot(\theta_1)|\Delta\theta \tag{F13}$$

and $$\Delta E_2 = E|\cot(\theta_2)|\Delta\theta \tag{F14}$$, respectively.

Since $|\cot(\theta_2)|$ is monotonically decreasing in the given θ range and $\theta_2 > \theta_1$, $$|\cot(\theta_2)| < |\cot(\theta_1)| \tag{F15}$$

and thus $$\Delta E_2 < \Delta E_1. \tag{F16}$$

That is, the energy error of the second order is smaller than the energy error of the first order. Therefore, the energy resolution is higher for the second order than for the first order. A user of the computer system 100 (cf. FIG. 1) may provide a higher diffraction order as an input to the system 100 via a user interface in case the system is supposed to also provide intensity values for higher diffraction order profile ensembles.

Another advantage can be the intensity reduction by higher orders. A wave-length dispersive x-ray spectrometer is using high power excitation sources to mitigate the intensity losses by the monochromatization of the analytical signal coming from the sample, and to improve the sensitivity for low concentration elements (traces). However, sample analysts need to determine the concentration of sample components from trace level to very high concentrations. However, the dynamic range of the detector is limited. Typically, different fluorescence lines are used for low and high concentrations or the generator power is reduced. Alternatively, a filter may be added between the x-ray tube and sample. However, such changes in excitation or detection increase the measurement time. Since the higher order intensities (contribution areas) are simultaneously determined with the first order contribution area by the herein disclosed pulse height spectrum fitting approach, such higher order intensities can be used to gather reduced intensities without changing the excitation and thus without increasing the measurement time.

Figure 13:
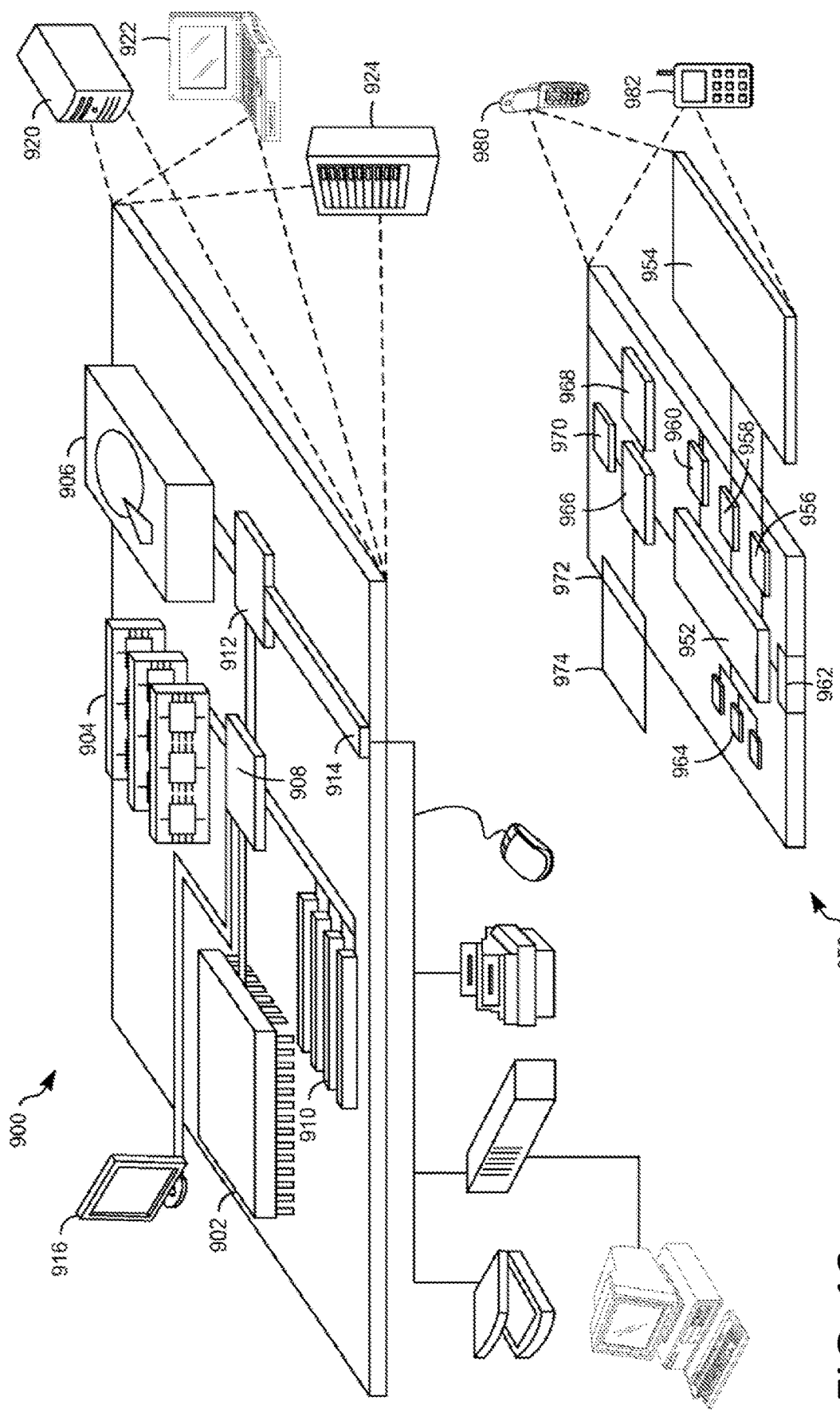
FIG. 13 is a diagram that shows an example of a generic computer device and a generic mobile computer device, which may be used with the techniques described herein.

FIG. 13 is a diagram that shows an example of a generic computer device 900 and a generic mobile computer device 950, which may be used with the techniques described here. In some embodiments, computing device 900 may relate to system 100 (cf. FIG. 1). As mentioned earlier, such a computer device 900 may be implemented as an integrated component of a wave-length dispersive X-ray fluorescence spectrometer. Computing device 950 is intended to represent various forms of mobile devices, such as personal digital assistants, cellular telephones, smart phones, and other similar computing devices. In the context of this disclosure the computing device 950 may provide I/O means for a user to interact with the computing device 950 (e.g., for selecting the diffraction orders used for the analysis of the sample). The components shown here, their connections and relationships, and their functions, are meant to be exemplary only, and are not meant to limit implementations described and/or claimed in this document.

Computing device 900 includes a processor 902, memory 904, a storage device 906, a high-speed interface 908 connecting to memory 904 and high-speed expansion ports 910, and a low-speed interface 912 connecting to low-speed bus 914 and storage device 906. Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high-speed interface 908. In other implementations, multiple processors and/or multiple buses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, or memory on processor 902.

The high-speed controller 908 manages bandwidth-intensive operations for the computing device 900, while the low-speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provide in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 984 may also be provided and connected to device 950 through expansion interface 982, which may include, for example, a SIMM (Single In Line Memory Module) card interface. Such expansion memory 984 may provide extra storage space for device 950, or may also store applications or other information for device 950. Specifically, expansion memory 984 may include instructions to carry out or supplement the processes described above, and may include secure information also. Thus, for example, expansion memory 984 may act as a security module for device 950, and may be programmed with instructions that permit secure use of device 950. In addition, secure applications may be provided via the SIMM cards, along with additional information, such as placing the identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 984, or memory on processor 952, that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, WiFi, or other such transceiver (not shown). In addition, GPS (Global Positioning System) receiver module 980 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smart phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

The invention claimed is:

1. A computer-implemented method for estimating peak intensities in pulse height spectra obtained by wave-length dispersive X-ray fluorescence spectrometers, comprising:

receiving a pulse height spectrum obtained by a multi-channel analyzer of a wavelength-dispersive X-ray fluorescence spectrometer from a sample;

generating a pulse height spectrum model with a plurality of diffraction order profile ensembles by:

creating a plurality of diffraction order profiles with predefined profile shapes at photon energy positions corresponding to respective diffraction orders of a monochromator of the spectrometer, wherein widths of the diffraction profiles are determined by using a calibrated width model reflecting dependencies of the widths on respective energy positions and total incoming count rates of a detector of the spectrometer, and wherein relative positions of the diffraction order profiles are determined by their respective energies and a pulse-height-to-energy mapping;

for created diffraction order profiles where the corresponding photon energy is higher than an edge energy of detector material of the detector, adding a respective escape profile at the position of the photon energy of the diffraction order profile diminished by the fluorescence energy of the photon escaped from the detector material, wherein the intensity of the escape profile is determined by using a calibrated escape intensity model reflecting dependencies of the intensity on respective energy positions;

wherein a particular diffraction order profile ensemble comprises all generated profiles associated with the respective diffraction order;

adjusting pulse-height-to-energy-mapping parameters and contribution area of each diffraction order profile ensemble of the pulse height spectrum model using a fitting algorithm to minimize a difference between the pulse height spectrum model and the received pulse height spectrum; and providing the contribution area of a first order profile ensemble as the intensity at the energy to be determined by the wavelength-dispersive X-ray fluorescence spectrometer.

2. The method of claim 1, wherein generating a pulse height spectrum model further comprises any of:

adding a pile-up profile to the first order diffraction profile wherein the intensity of the pile-up is determined by using a calibrated pile-up intensity model reflecting dependencies of the intensity on respective energy positions and total incoming count rates of the detector;

if the detector is a gas detector, adding one or more aging profiles to the pulse height spectrum model by copying and shifting the generated diffraction order profile ensembles by a calibrated energy offset, with adjusting further comprising scaling the intensities of the generated diffraction order profile ensembles in relation to the intensities of the respective aging profiles; and adding to one or more generated profiles of the pulse height spectrum model corresponding one or more shelf contribution profiles as constant intensity values starting at the respective generated profile position and extending to a defined lower detector dependent energy, wherein the constant intensity values are determined by using a calibrated shelf intensity model reflecting dependencies of the intensity on respective energy positions.

3. The method of claim 1, wherein the fitting algorithm is a least-squares fitting algorithm and wherein starting values for the contribution areas of the diffraction order profile ensembles are obtained by integrating the obtained pulse height spectrum between 0.5 to 1.5 times the respective diffraction order energy, and wherein one or more of the following constraints are set: box-constraints for the pulse-height-to-energy-mapping parameters to allow only non-substantial changes over previously determined parameters, non-negative constraints for the contribution areas of the diffraction order profile ensembles.

4. The method of claim 1, wherein the predefined profile shape is selected from any of: Lorentzian, Gaussian, Voigt and pseudo-Voigt shape.

5. The method of claim 1, wherein providing further comprises providing the contribution area of at least a second order profile ensemble for improving a resolution of a goniometer measurement performed by the wavelength-dispersive X-ray fluorescence spectrometer with an energy error of the second order profile ensemble being smaller than the energy error of the first order profile ensemble.

6. The method of claim 1, wherein the adjusting and providing steps remove artifact contributions of characteristic emission lines from higher orders of the pulse height spectrum in a goniometer measurement performed by the spectrometer.

7. The method of claim 1, wherein the adjusting and providing steps reduce an influence of Bremsstrahlung background from higher orders of the pulse height spectrum.

8. The method of claim 2, wherein the intensity at the to-be-determined energy is a sum of first order profile intensity, escape profile intensity and the intensity of the pile-up profile multiplied by a correction factor.

9. A computer system for estimating peak intensities in pulse height spectra obtained by wave-length dispersive x-ray fluorescence spectrometers, comprising:

an interface adapted to receive a pulse height spectrum obtained by a multi-channel analyzer of a wavelength-dispersive X-ray fluorescence spectrometer from a sample;

a model generator adapted to generate a pulse height spectrum model with a plurality of diffraction order profile ensembles by:

creating a plurality of diffraction order profiles with predefined profile shapes at photon energy positions corresponding to respective diffraction orders of a monochromator of the spectrometer, wherein widths of the diffraction profiles are determined by using a calibrated width model reflecting dependencies of the widths on respective energy positions and total incoming count rates of a detector of the spectrometer, and wherein relative positions of the diffraction order profiles are determined by their respective energies and a pulse-height-to-energy mapping;

for created diffraction order profiles where the corresponding photon energy is higher than an edge energy of detector material of the detector, adding a respective escape profile at the position of the photon energy of the diffraction order profile diminished by the fluorescence energy of the photon escaped from the detector material, wherein the intensity of the escape profile is determined by using a calibrated escape intensity model reflecting dependencies of the intensity on respective energy positions;

wherein a particular diffraction order profile ensemble comprises all generated profiles associated with the respective diffraction order;

a model adjustment module adapted to adjust pulse-height-to-energy-mapping parameters and contribution area of each diffraction order profile ensemble of the pulse height spectrum model using a fitting algorithm to minimize difference between the pulse height spectrum model and the received pulse height spectrum; and and intensity module adapted to provide the contribution area of first order profile ensemble as the intensity of the energy to be determined by the wavelength-dispersive X-ray fluorescence spectrometer.

10. The system of claim 9, wherein the model generator is further adapted to generate a pulse height spectrum model by using any of:

adding a pile-up profile to the first order diffraction profile wherein the intensity of the pile-up is determined by using a calibrated pile-up intensity model reflecting dependencies of the intensity on respective energy positions and total incoming count rates of the detector;

if the detector is a gas detector, adding one or more aging profiles to the pulse height spectrum model by copying and shifting the generated diffraction order profile ensembles by a calibrated energy offset, with adjusting further comprising scaling the intensities of the generated diffraction order profile ensembles in relation to the intensities of the respective aging profiles; and adding to one or more generated profiles of the pulse height spectrum model corresponding one or more shelf contribution profiles as constant intensity values starting at the respective generated profile position and extending to a defined lower detector dependent energy, wherein the constant intensity values are determined by using a calibrated shelf intensity model reflecting dependencies of the intensity on respective energy positions.

11. The system of claim 9, wherein the intensity module is further adapted to provide the contribution area of at least a second order profile ensemble for improving a resolution of a goniometer scan performed by the wavelength-dispersive X-ray fluorescence spectrometer with an energy error of the second order profile ensemble being smaller than the energy error of the first order profile ensemble.

12. The system of claim 9, wherein the adjustment module and the intensity module, when performing the adjusting and providing steps, remove artifact contributions of characteristic emission lines from higher orders of the pulse height spectrum in a goniometer measurement performed by the spectrometer.

13. The system of claim 9, wherein the fitting algorithm is a least-squares fitting algorithm, and wherein starting values for the contribution areas of the diffraction order profile ensembles are obtained by integrating the obtained pulse height spectrum between 0.5 to 1.5 times the respective diffraction order energy, and wherein one or more of the following constraints are set: box-constraints for the pulse-height-to-energy-mapping parameters to allow only non-substantial changes over previously determined parameters, non-negative constraints for the contribution areas of the diffraction order profile ensembles.

14. A computer program product for estimating peak intensities in pulse height spectra obtained by wave-length dispersive X-ray fluorescence spectrometers, with computer readable instructions that, when loaded into a memory of a computing device and executed by at least one processor of the computing device, causes the computing device to receive a pulse height spectrum obtained by a multi-channel analyzer of a wavelength-dispersive X-ray fluorescence spectrometer from a sample;

generate a pulse height spectrum model with a plurality of diffraction order profile ensembles by:

creating a plurality of diffraction order profiles with predefined profile shapes at photon energy positions corresponding to respective diffraction orders of a monochromator of the spectrometer, wherein widths of the diffraction profiles are determined by using a calibrated width model reflecting dependencies of the widths on respective energy positions and total incoming count rates of a detector of the spectrometer, and wherein relative positions of the diffraction order profiles are determined by their respective energies and a pulse-height-to-energy mapping;

for created diffraction order profiles where the corresponding photon energy is higher than an edge energy of detector material of the detector, adding a respective escape profile at the position of the photon energy of the diffraction order profile diminished by the fluorescence energy of the photon escaped from the detector material, wherein the intensity of the escape profile is determined by using a calibrated escape intensity model reflecting dependencies of the intensity on respective energy positions;

wherein a particular diffraction order profile ensemble comprises all generated profiles associated with the respective diffraction order;

adjust pulse-height-to-energy-mapping parameters and contribution area of each diffraction order profile ensemble of the pulse height spectrum model using a fitting algorithm to minimize a difference between the pulse height spectrum model and the received pulse height spectrum; and provide the contribution area of a first order profile ensemble as the intensity at the energy to be determined by the wavelength-dispersive X-ray fluorescence spectrometer.

15. The computer program product of claim 14, wherein the computer readable instructions, when loaded into the memory of the computing device and executed by at least one processor of the computing device, cause the computing device to generate a pulse height spectrum model by executing any of:

adding a pile-up profile to the first order diffraction profile wherein the intensity of the pile-up is determined by using a calibrated pile-up intensity model reflecting dependencies of the intensity on respective energy positions and total incoming count rates of the detector;

if the detector is a gas detector, adding one or more aging profiles to the pulse height spectrum model by copying and shifting the generated diffraction order profile ensembles by a calibrated energy offset, with adjusting further comprising scaling the intensities of the generated diffraction order profile ensembles in relation to the intensities of the respective aging profiles; and adding to one or more generated profiles of the pulse height spectrum model corresponding one or more shelf contribution profiles as constant intensity values starting at the respective generated profile position and extending to a defined lower detector dependent energy, wherein the constant intensity values are determined by using a calibrated shelf intensity model reflecting dependencies of the intensity on respective energy positions.

16. The computer program product of claim 14, wherein the fitting algorithm is a least-squares fitting algorithm and wherein starting values for the contribution areas of the diffraction order profile ensembles are obtained by integrating the obtained pulse height spectrum between 0.5 to 1.5 times the respective diffraction order energy, and wherein one or more of the following constraints are set: box-constraints for the pulse-height-to-energy-mapping parameters to allow only non-substantial changes over previously determined parameters, non-negative constraints for the contribution areas of the diffraction order profile ensembles.

17. The computer program product of claim 14, wherein the computer readable instructions, when loaded into the memory of the computing device and executed by at least one processor of the computing device, cause the computing device to:
provide the contribution area of at least a second order profile ensemble for improving a resolution of a goniometer measurement performed by the wavelength-dispersive X-ray fluorescence spectrometer with an energy error of the second order profile ensemble being smaller than the energy error of the first order profile ensemble.

18. The computer program product of claim 14, wherein the computer readable instructions, when loaded into the memory of the computing device and executed by at least one processor of the computing device, cause the computing device to:
remove artifact contributions of characteristic emission lines from higher orders of the pulse height spectrum in a goniometer measurement performed by the spectrometer.

19. The computer program product of claim 14, wherein the computer readable instructions, when loaded into the memory of the computing device and executed by at least one processor of the computing device, cause the computing device to:
reduce an influence of Bremsstrahlung background from higher orders of the pulse height spectrum.

20. The computer program product of claim 15, wherein the intensity at the to-be-determined energy is a sum of first order profile intensity, escape profile intensity and the intensity of the pile-up profile multiplied by a correction factor.

* * * * *

UNITED STATES PATENT AND TRADEMARK OFFICE
CERTIFICATE OF CORRECTION

PATENT NO. : 11,678,803 B1
APPLICATION NO. : 18/160656
DATED : June 20, 2023
INVENTOR(S) : Nitsche It is certified that error appears in the above-identified patent and that said Letters Patent is hereby corrected as shown below:

On the Title Page

Column 1, Item (73), in "Assignee", Line 1, delete "Broker" and insert -- Bruker --, therefor.

Signed and Sealed this
Fourteenth Day of November, 2023

Katherine Kelly Vidal
Director of the United States Patent and Trademark Office